(12) United States Patent
Korant

(10) Patent No.: US 6,649,644 B1
(45) Date of Patent: Nov. 18, 2003

(54) METHOD OF TREATING HIV INFECTION BY COMBINED USE OF A CYTOTOXIC AGENT AND A NON-NUCLEOSIDE REVERSE TRANSCRIPTASE INHIBITOR

(75) Inventor: Bruce D. Korant, Wilmington, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/416,431

(22) Filed: Oct. 12, 1999

Related U.S. Application Data

(60) Provisional application No. 60/103,922, filed on Oct. 13, 1998.

(51) Int. Cl.⁷ ............... A61K 31/415; A61K 31/535; A61K 31/35; A61K 31/335
(52) U.S. Cl. ............ 514/405; 514/230.5; 514/228.8; 514/229.5; 514/453; 514/463
(58) Field of Search ................ 514/269, 561, 514/613, 405, 230.5, 228.8, 229.5, 453, 463

(56) References Cited

U.S. PATENT DOCUMENTS

| | | | |
|---|---|---|---|
| 4,556,654 A | | 12/1985 | Showalter et al. |
| 4,608,439 A | | 8/1986 | Johnson et al. |
| 4,672,129 A | | 6/1987 | Beylin et al. |
| 5,519,021 A | | 5/1996 | Young et al. |
| 5,635,523 A | * | 6/1997 | Kempf et al. ........... 514/365 |
| 5,663,169 A | | 9/1997 | Young et al. |
| 5,665,720 A | | 9/1997 | Young et al. |
| 5,756,537 A | * | 5/1998 | Gill |

FOREIGN PATENT DOCUMENTS

| | | |
|---|---|---|
| EP | 617968 A1 | 5/1994 |
| WO | 9845276 | 10/1998 |

OTHER PUBLICATIONS

Merluzzi et al., Science 250:1411–1413 (1990).*
Leteurtre et al., J. Natl. Cancer Inst. (1994), 86(16), 1239–44.*
Mayers et al., 37th Interscience Conference on Antimicrobial Agents and Chemotherapy (Sep. 28, 1997) p. 275.*
Carpenter et al., 1997, JAMA, 277, 1962–1969.
Meyaard et al., 1992, Science, 257, 217–219.
Ameisen et al, 1995, Trends Cell Biol., 5, 27–32.
Wong et al., 1991, PNAS, 88, 4372–4375.
Sandstrom et al., 1993, AIDS Res. and Human Retro., 9, 1107–1113.
Katsikis et al., 1995, J. Exp. Med., 181, 2029–2036.
Wu et al., 1995, Jpn. J. Med. Sci. Biol., 48, 79–87.
Gougeon et al., 1996, J. Immunol., 198, 87–99.
Hashimoto, K. et al., 1997, AIDS Res. and Human Retro., 13, 193–199.
Prati E. et al., 1997, AIDS Res. and Human Retro., 13, 1501–1508.
Reed, J., 1994, J. Cell Biol. 124, 1–6.
Liles, W. C., 1997, Curr. Opin. Inf. Dis., 10, 165–170.
Matsuyama et. al., 1989, J. Virol., 63, 2504–2509.
Woloschak et al., 1997, Bioch. Bphys. Acta, 1351, 105–110.
Zhang et al., 1997, AIDS, 11, 1219–1225.
Levine et al., 1991, JAMA, 266, 84–88.
Zanussi. et al., 1996, Aids Res. and Human Retro. 12, 1703–1707.
Carpenter et al., 1997, JAMA, 277, 1962–1969.
Gougeon et al., 1996, J. Immunol., 198, 87–99.
Hashimoto, K. et al., 1997, AIDS Res. and Human Retro., 13, 193–199.
Matsuyama et. al., 1989, J. Virol., 63, 2504–2509.
Woloschak et al., 1997, Bioch. Bphys. Acta, 1351, 105–110.
Levine et al., 1991, JAMA, 266, 84–88.
Zanussi. et al., 1996, Aids Res. and Human Retro. 12, 1703–1707.

\* cited by examiner

*Primary Examiner*—Sreeni Padmanabhan
*Assistant Examiner*—S. Jiang
(74) *Attorney, Agent, or Firm*—Samuel J. DuBoff; Christine Goddard

(57) ABSTRACT

This invention relates to a method of treating human immunodeficiency virus (HIV) infection in a mammal comprising administering to the mammal a therapeutically effective amount of a combination of: (i) at least one cytotoxic agent and (ii) at least one non-nucleoside reverse transcriptase HIV inhibitor (NNRTI). This invention also relates to a method of treating chronic viral infections comprising administering to the mammal a therapeutically effective amount of a combination of: (i) at least one cytotoxic agent and (ii) at least one antiviral agent.

1 Claim, No Drawings

METHOD OF TREATING HIV INFECTION BY COMBINED USE OF A CYTOTOXIC AGENT AND A NON-NUCLEOSIDE REVERSE TRANSCRIPTASE INHIBITOR

This application claims the benefit of U.S. provisional appliction No. 60/103,922, filed Oct. 13, 1998.

FIELD OF THE INVENTION

This invention relates to a method of treating human immunodeficiency virus (HIV) infection in a mammal comprising administering to the mammal a therapeutically effective amount of a combination of: (i) at least one cytotoxic agent and (ii) at least one non-nucleoside reverse transcriptase HIV inhibitor (NNRTI). This invention also relates to a method of treating chronic viral infections comprising administering to the mammal a therapeutically effective amount of a combination of: (i) at least one cytotoxic agent and (ii) at least one antiviral agent.

BACKGROUND OF THE INVENTION

HIV infections are at the present time routinely treated with combinations of antiviral drugs (Carpenter, C. et al. Antiretroviral therapy for HIV infection in 1997. JAMA 277, 1962, 1997). The results are beneficial for many patients, with a pronounced drop in viral load, increase in lymphocyte populations, reduction in opportunistic infections and a doubling of time of progression to serious illness and/or death. However, the treatments are done chronically, and can lose effectiveness over time, in part because few if any individuals are cured. Usually HIV persists in cells in the immune system as well as in nervous tissue, and the residual virus may, after months or years of persistence and low-level replication, develop resistance to the drugs and reemerge. At that time, a new set of antivirals is substituted for the initial therapy, and the virus may again be suppressed, although frequently less effectively. The decline in circulating, functional lymphocytes is not only characteristic of HIV infection, it is believed to play a central role in the loss of immunity in the patients (Meyaard, L. et al. Programmed death of T-cells in HIV-1 infection. Science 257, 217, 1992; Ameisen, J. et al. Relevance of apoptosis to AIDS pathogenesis. Trends Cell Biol. 5, 27, 1995). For example, CD4+lymphocytes, in which the HIV preferentially replicates, may decline by 90–99% in the final stage of the HIV infection. The current measure of success of conventional HIV antiviral therapy is to protect these cells and restore their numbers and functions. HIV-infected cells are known to be more susceptible to the toxic effects of cytocidal drugs, certain cytokine proteins, radiation and other damaging agents, compared to their uninfected counterparts (Wong, G. et al. TNF alpha selectively sensitizes HIV-infected cells to heat and radiation. PNAS 88, 4372, 1991; Sandstrom, P. et al. HIV gene expression enhances T-cell susceptibility to $H_2O_2$-induced apoptosis. AIDS Res. and Human Retro. 9, 1107, 1993; Katsikis, P. et al. Fas antigen stimulation induces marked apoptosis of T-lymphocytes in HIV-infected individuals. J. Exp. Med. 181, 2029, 1995; Wu X. et al. Apoptosis of HIV-infected cells following treatment with Sho-saiko To and its components. Jpn. J. Med. Sci. Biol. 48, 79, 1995; Gougeon, M. et al. Programmed cell death in peripheral lymphocytes from HIV-infected persons. J. Immunol. 156, 3509, 1996; Hashimoto, K. et al. Stavudine selectively induces apoptosis in HIV type 1-infected cells. AIDS Res. and Human Retro. 13, 193, 1997; Prati, E. et al. Study of spontaneous apoptosis in HIV and patients: Correlation with clinical progression and T-cell loss. AIDS Res. and Human Retro. 13, 1501, 1997). The explanation of the events leading to enhanced death of HIV-infected cells is controversial, but it is clear that the infected cells become depleted of certain broadly acting anti-death proteins normally present in the cells, including the well-known bcl-2 family of proteins (Reed, J. Bcl-2 and the regulation of programmed cell death. J. Cell Biol. 124, 1, 1994). A decrease of bcl-2 typically leads to onset of programmed cell death, or apoptosis, a phenomenon widely observed in HIV-infected cells in vivo and in vitro, both spontaneously and following various external stresses (Liles, W. C. Apoptosis-role in infection and inflammation. Curr. Opin. Inf. Dis. 10, 165, 1997).

The tendency of HIV-infected cells to die or be selectively killed by toxic treatments is known. However, prior to this invention this knowledge has not been exploited for therapeutic purposes. The reason for this is that virtually all cytotoxic treatments cause rapid activation of HIV transcription, leading to a large burst of new progeny virus which proceeds to infect surrounding healthy cells and spread the infection. There has been speculation that the unusually high level of cell killing (for a retrovirus) is part of the biology of HIV, leading to greater spread of the infection (Matsuyama, T. et al. Cytocidal effect of TNF on cells chronically infected with HIV: Enhancement of HIV replication. J. Virol. 63, 2504, 1989; Woloschak, G. et al. HIV expression in dying cells. Bioch. Bphys. Acta 1351, 105, 1997; Zhang, Y. et al. Induction of apoptosis by primary HIV-1 isolates correlates with productive infection in peripheral blood mononuclear cells. AIDS 11, 1219, 1997). Standard antiviral drugs, such as azidothymidine, are not powerful enough to keep HIV in check if infected cells are exposed to a potent cytotoxic drug. This has severely complicated efforts to use chemotherapy to control cancers in HIV-infected individuals (Levine, A. et al. Low-dose chemotherapy with CNS prophylaxis and Zidovudine maintenance in AIDS-related lymphoma. JAMA 266, 84, 1991; Zanussi, S. et al. Effects of anti-neoplastic chemotherapy on HIV disease. AIDS Res. and Human Retro. 12, 1703, 1996).

A number of new antiviral agents have been developed, such as efavirenz, which potently inhibit the reverse transcriptase of the virus. We have discovered in studies in cell culture that such a potent reverse transcriptase inhibitor, combined with a standard cytotoxic drug such as etoposide, can inhibit HIV replication, while infected cells are selectively killed. Surprisingly, a different class of anti-HIV agents, namely protease inhibitors, failed to permit eradication of infected cells.

SUMMARY OF THE INVENTION

One object of the present invention is to provide a novel method of treating human immunodeficiency virus (HIV) infection in a mammal comprising administering to the mammal a therapeutically effective amount of a combination of: (i) at least one cytotoxic agent, and (ii) at least one non-nucleoside reverse transcriptase HIV inhibitor (NNRTI).

Another object of the present invention is to provide a novel method of treating chronic viral infections including, but not limited to, those caused by herpesvirus, cytomegalovirus, hepatitis B virus, hepatitis C virus, and varicella-zoster by selectively eradicating the virally infected cells, comprising administering to the mammal a therapeutically effective amount of: (i) at least one cytotoxic agent, and (ii) and at least one antiviral agent selective for the chronic virus.

These and other objects, which will become apparent during the following detailed description, have been achieved by the inventor's discovery that the administration of a cytotoxic agent, component (i) in combination with a NNRTI, component (ii) results in an unexpected, selective eradication of HIV infected cells.

DETAILED DESCRIPTION OF THE INVENTION

Preferred embodiments of the invention have been chosen for purposes of illustration and description, but are not intended in any way to restrict the scope of the invention.

In a first embodiment, the present invention provides a method of treating human immunodeficiency virus (HIV) infection in a mammal comprising administering in combination to the mammal a therapeutically effective amount of: (i) a cytotoxic agent and (ii) at least one non-nucleoside reverse transcriptase HIV inhibitor (NNRTI).

In a preferred embodiment, the NNRTI is efavirenz.

In another preferred embodiment, the cytotoxic agent is losoxantrone.

In a more preferred embodiment, cytotoxic agent is losoxantrone, and the NNRTI is efavirenz.

In another embodiment, the present invention provides a method of treating chronic viral infections including, but not limited to, those caused by herpesvirus types I and II, cytomegalovirus, hepatitis B virus, hepatitis C virus, and varicella-zoster by selectively eradicating the virally infected cells, comprising administering to the mammal a therapeutically effective amount of: (i) at least one cytotoxic agent, and (ii) and at least one antiviral agent selective for the chronic virus.

The cytotoxic compound losoxantrone is described in U.S. Pat. No. 4,556,654, 4,608,439, and 4,672,129, such disclosures are hereby incorporated by reference.

The non-nucleoside reverse transcriptase inhibitor of HIV, efavirenz, is described in U.S. Pat. No. 5,519,021, 5,663,169, and 5,665,720, such disclosures are hereby incorporated by reference.

As used herein, the term "non-nucleoside reverse transcriptase HIV inhibitor" (NNRTI) includes, but is not limited to, delavirdine, (Pharmacia and Upjohn U90152S), efavirenz (DuPont Pharmaceuticals), nevirapine (Boehringer Ingelheim), RO 18,893 (Roche), trovirdine (Lilly), MKC-442 (Triangle), HBY 097 (Hoechst), ACT (Korean Research Institute), UC-781, (Rega Institute), UC-782, (Rega Institute), RD4-2025 (Tosoh Co. Ltd. ), MEN 10970 (Menarini Farmacuetici), TIBO derivatives, BI-RG-587, L 697,661, LY 73497, and loviride (Jannsen). additional examples include (−)-6-chloro-4-cyclopropylethynyl-4-trifluoromethyl-3,4-dihydro-2(1H)-quinazolinone), "Compound A"; (+)-4-Cyclopropylethynyl-5,6-difluoro-4-trifluoromethyl-3,4-dihydro-2(1H)-quinazolinone), "Compound B"; (+)-4-cyclopropylethenyl-5,6-difluro-4-trifluoromethyl-3,4-dihydro-2(1H)-quinazolinone, "Compound C"; and (−)-6-chloro-4-E-cyclopropylethenyl-4-trifluoromethyl-3,4-dihydro-2(1H)-quinazolinone, "Compound D" (DuPont Pharmaceuticals), NNRTIs disclosed in U.S. application Ser. No. 09/056820, the disclosure of which is hereby incorporated by reference.

As used herein, the term "cytotoxic agent" includes, but is not limited to, altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, etoposide, teniposide, vinblastine, vincristine, vinorelbine, procarbazine, asparaginase, pegaspargase, octreotide, estramustine, hydroxyurea.

"Therapeutically effective amount" is intended to include an amount of a compound or an amount of a combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, eradication of HIV-infected cells) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other non-additive beneficial effect of the combination compared with the individual components.

By "administered in combination", "combination", or "combined" when referring to component (i) and component (ii) of the present invention, it is meant that the components are administered concurrently to the cell or mammal being treated. When administered in combination each component may be administered at the same time or sequentially in any order or at different points in time. Thus, component (i) and component (ii) may be administered separately but sufficiently closely in time so as to provide the desired HIV-infected cell eradication effect.

As used herein, "selective" refers to the ability of a particular drug or antiviral protein to target a cell that is infected with a specific virus.

As used herein, "antiviral agent" includes, but is not limited to, lamivudine (3TC), famcyclovir, lobucavir, adevovir, interferon alpha, interferon alpha plus virazole, acylovir, valacyclovir, sorivudine, iododeoxyuridine, gancyclovir, foscavir, cidofovir, fomivirsen, and netivudine.

Pharmaceutical kits useful for the inhibition of HIV and treatment of HIV infection, which comprise a therapeutically effective amount of a pharmaceutical composition comprising a compound of component (i) and one or more compounds of component (ii), in one or more sterile containers, are also within the ambit of the present invention. Sterilization of the container may be carried out using conventional sterilization methodology well known to those skilled in the art. Component (i) and component (ii) may be in the same sterile container or in separate sterile containers. The sterile containers of materials may comprise separate containers, or one or more multi-part containers, as desired. Component (i) and component (ii), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

In order to test whether some external death stimuli, which are independent of bcl-2 (Reed, 1994), may not selectively kill HIV-infected cells, we exposed uninfected and HIV-infected cells to various chemical toxins, including losoxantrone, bisnafide, etoposide and hydroxyurea. Etoposide is the only one of these agents to have previously been shown to be blocked by bcl-2 (Reed, 1994). In cultured cells expressing an increased level of bcl-2, we found a 3 to 5-fold resistance to the actions of etoposide and losoxantrone, but not bisnafide. Therefore, we proceeded to examine whether either losoxantrone or etoposide were able to selectively kill HIV-infected cells. Table 1 shows the results of such an experiment.

TABLE 1

Toxicity of compounds for human
T-lymphocytes (MT-2) infected with HIV-1.

| Compound | Viable Cells<br>−HIV | (% Remaining)<br>+HIV |
|---|---|---|
| None | 83 | 70 |
| losoxantrone (10 nM) | 68 | 4 |
| etoposide (100 nM) | 71 | 12 |
| efavirenz(10 nM) | 81 | 82 |

*MTT assay - see Example 1

After 24 hours in presence of the cytotoxic chemicals, losoxantrone had killed infected cells to a 5-fold greater extent than uninfected lymphocytes, while etoposide was 6-fold more toxic to infected cells. Efavirenz showed no toxicity to either cell population at the concentration shown, 10 nM.

Comparing cell survival for infected vs. control cells indicates there is a range of losoxantrone concentrations that show selectivity for infected cells from 0.1 to 10 nM. At 10 nM or greater, there is evidence of substantial toxicity to uninfected cells, but selectivity is still not entirely lost.

Previous studies from several laboratories indicated that although selective killing of HIV-infected cells follows a variety of toxic treatments, it was always accompanied by a large burst of HIV transcription and release of progeny virus particles, which could then proceed to infect and replicate in neighboring cells (Wong, 1991; Matsuyama, 1989; Woloschak, 1997; Zhang, 1997; Levine, 1991; and Zanussi, 1996). This phenomenon has made dealing with solid tumors or leukemias/lymphomas very difficult in HIV-positive individuals (Levine, 1991; and Zanussi, 1996), in part because early HIV inhibitors which could be co-administered had relatively low potency to inhibit the virus replication and spread, particularly after a strong induction by a cytotoxic drug. Recently, the situation has changed, with introduction of potent antivirals directed at the HIV protease or reverse transcriptase (Carpenter, 1997).

In order to selectively kill infected cells without an accompanying induction of HIV, we combined a very potent antiviral with a cytotoxic drug. The experimental protocol we adopted to monitor eradication of infected cells is based on the principle that surviving infected cells will produce sufficient HIV to initiate a new wave of infection in naive cells, in a co-cultivated environment. This is sometimes called an infectious center assay procedure, and has been used for HIV and other viruses (The Molecular Biology of Poliovirus. F. Koch and G. Koch, eds. p307. Springer Verlag, Vienna 1985).

Minimal doses of the compounds were employed in our trial. For the cytotoxic drugs losoxantrone and etoposide, a dose was selected which would be toxic to 90% or greater of HIV-infected cells, but non-toxic to uninfected cells. For the anti-retrovirals, namely the reverse transcriptase inhibitor efavirenz or the cyclic urea HIV protease inhibitor [4R-(4α, 5α, 6β, 7β]-1,3-bis (3-aminophenylmethyl] hexahydro-5,6-dihydroxy-4,7-bis (phenlymethyl-2H-1,3-diazepin-2-one dimethylsulfonate ("Compound E", DuPont/Triangle), the dose chosen was approximately the $IC_{90}$ for HIV replication. This minimal dose was used so that further losses of HIV infectivity due to application of the cytotoxic drug could easily be monitored; in a clinical setting the highest tolerated antiviral dose would be preferred.

Freshly isolated human blood lymphocytes and monocytes were infected with HIV-1 (RF strain) and then incubated for an additional 3 days in the presence of compounds alone or in combinations or left untreated. At the end of 4 days, the infected cells were briefly centrifuged. The supernatant was collected and used to titer HIV p24, using an enzyme-linked immunosorbent assay (ELISA). The cell pellets were washed two times with medium lacking any inhibitors, and the washed human peripheral blood mononuclear cells (PBMCs) were mixed 1:1 with MT-2 lymphocytes and incubated for an additional 4 days absent any inhibitors. All cells were then removed by centrifugation and the supernatant was again assayed for p24 levels by ELISA.

As shown in Table 2 below, losoxantrone, efavirenz and Compound E, at the concentrations shown, caused only small changes in the level of HIV p24 after either 4 or 8 days.

TABLE 2

Effects of compounds on HIV replication (day 4)
and infectious centers (day 8) using isolated human PBMCs.

| Compound | HIV<br>Replication<br>(Day 4)* | Infectious<br>Centers<br>(Day 8)* |
|---|---|---|
| None | $8 \times 10^4$ | $1 \times 10^5$ |
| losoxantrone (10 nM) | $2 \times 10^5$ | $7 \times 10^5$ |
| efavirenz (10 nM) | $1.5 \times 10^4$ | $2 \times 10^5$ |
| Compound E (100 nM) | $2.5 \times 10^4$ | $3.5 \times 10^5$ |
| losoxantrone & efavirenz | $6 \times 10^3$ | $1.8 \times 10^2$ |
| losoxantrone & Compound E | $1.7 \times 10^5$ | $8 \times 10^4$ |

*p24 pg/mL

Losoxantrone(10 nM) caused a 3 to 7-fold increase in p24 titers, while the two antivirals caused about a 80% reduction on day 4, which had recovered by day 8, after compounds were removed. Only the combination of a cytotoxic drug with efavirenz caused a substantial loss (1 log or greater) both at days 4 and 8. It was noted that even after removal of both compounds and 4 further days of incubation, there was little or no p24 production by the MT-2 cells, including a large loss of infectious centers among the PBMCs. In some experiments, there was no p24 detected above background at day 8 in the cells treated with efavirenz and losoxantrone. When etoposide was substituted for losoxantrone, the results were very similar (not shown). In comparison, there was little effect on p24 production by combining the protease inhibitor, Compound E with a cytotoxic drug.

Recent reports have indicated a synergy between a reverse transcriptase inhibitor, didanosine (DDI) and a cytotoxic agent, hydroxyurea (HU) (Lori, F. et al. Hydroxyurea as an inhibitor of HIV-1 replication. Science 266, 801, 1994; Lori, F. et al. Combination of a drug targeting the cell with a drug targeting the virus controls HIV-1 resistance. AIDS Res. and Human Retro. 13, 1403, 1997). We therefore tested whether HU could be combined with efavirenz to eradicate infectious centers. A dose of HU was chosen which was shown to inhibit PBMC cell division by 3-fold (100 μM). However, the combination of efavirenz with that dose of HU failed to significantly reduce the number of infectious centers as shown in Table 3.

TABLE 3

Effects of losoxantrone and hydroxyurea on HIV replication and infectious centers in combination with efavirenz in isolated human PBMCs.

| Compound | HIV Replication (Day 4)* | Infectious Centers (Day 8)* |
|---|---|---|
| None | $1.2 \times 10^5$ | $2.5\ 10^5$ |
| losoxantrone & efavirenz | $3 \times 10^3$ | $1.2 \times 10^2$ |
| hydroxyurea & efavirenz | $4 \times 10^3$ | $1.6 \times 10^4$ |

*p24 pg/mL.

Leveraging the tendency of HIV-infected cells to die or be killed has been problematic because of the coincident burst of new HIV progeny upon exposure to cytocidal drugs, toxic cytokines or physical treatments (Wong, 1991; Matsuyma, 1989; Woloschak, 1997; Zhang, 1997; Levine, 1991; and Zanussi, 1996). First-generation antiretroviral agents were not powerful enough to hold the virus in check under such conditions, and the currently available protease inhibitors fail to permit the selective killing action by tumoricidals such as losoxantrone or etoposide (Table 2). However, the use of the potent reverse transcriptase inhibitor efavirenz allows coincident application of a cytotoxic drug, with subsequent loss of infectious centers and suppression of virus production (Table 2). The combined use of the two agents is thus able to effect what no combination of antivirals has so far: the selective elimination of infected cells. In the clinic, a non-cytotoxic dose (for uninfected cells, which constitute the majority of cells even in a patient with full-blown AIDS) of a cytocidal drug should lead to selective killing of infected cells, and coupled with potent inhibition of the virus by efavirenz, little or no spread of infection should occur.

A significant advantage of this invention's approach, which combines a cytotoxic agent with one or more non-protease inhibitor antiretrovirals, is expected to be a rapid improvement in patient health, with no need for repeated, long-term dosing. Infected cells and virus should be quickly eliminated and this could significantly reduce the cost of treatment, and make therapy much more widely available in developing countries. Also, the acute nature of our therapeutic approach should minimize the ability of HIV to develop resistance, which may occur with conventional treatment regimens (Carpenter, 1997).

EXAMPLES

The invention can be further understood by the following examples. These examples provide an illustration of embodiments of the invention and should not be construed to limit the scope of the invention that is set forth in the appended claims. In the following examples all methods described are conventional unless otherwise specified.

Example 1

Cytotoxicity Determination

Efavirenz stock solutions were dissolved in dimethylsulfoxide (DMSO) to 1 mg/mL and stored frozen at −20° C. Target human peripheral blood mononuclear cells (PBMCs) from normal HIV-seronegative donors were obtained by Ficoll-Hypaque gradient centrifugation of heparinized blood purchased from Biological Specialties Corp., Colmar, Pa. After washing the cells four times in phosphate buffered saline (PBS), pH 7.4, the cells were resuspended at a density of approximately $1\times10^{e6}$ cells/mL in RPMI with 20% fetal calf serum (FCS). Phytohemagglutinin (PHA) was added to a concentration of 5 μg/mL and IL-2 to a concentration of 30 units/mL. Cells were incubated at 37° C., 5% CO2 for 72 hours to induce blast transformation.

The concentration of the cytotoxic drugs losoxantrone, etoposide or hydroxyurea required to reduce cell viability by 50% ($TC_{50}$) was determined with or without virus infection. Graded concentrations of drug in RPMI (5% FCS) were added to a 96-well microtiter plate. $1\times10^{e5}$ cells were added per well. Cell control wells contained cells in RPMI only. Plates were incubated at 37° C., 5% CO2 for 3 days. The tetrazolium dye (3-4,5-dimethylthiazol-2yl)-2,5-diphenyltetrazolium bromide (MTT) was used to assess the number of viable cells. After the 3-day incubation period, 10 μL of MTT (5 mg/mL in 1×PBS) was added to each well. Following a 2 hour incubation at 37° C., 150 μL was removed from each well and 200 μL of 0.04 N HCl in isopropanol was added. The contents of each well were mixed and the quantity of reduced dye was measured by absorbance at 570 nm. The concentration of compound producing a 50% reduction in signal relative to the untreated cultures ($TC_{50}$) was determined.

Example 2

Viral P24 Measurement

Viral p24 produced by HIV-1 (RF) infected cells was quantified to determine the effects of a cytotoxic drug and efavirenz alone or in combination. On day one, $5.25\times10^{e6}$ donor PBMCs (stimulated by PHA/IL-2 for 72 hours in RPMI tissue culture medium were centrifuged at 1,000 rpm for 10 minutes and the supernatant fluid was decanted. Using 50% tissue culture infectious dose ($TCID_{50}$) estimated from the viral stock titration procedure (PRR 97-04), $5.25\times10^6$ PBMCs were infected with $5.2\times10^3$ $TCID_{50}$ of virus (M. O. I. ~0.001). Cells were resuspended, the virus stock added, and incubated at 37° C. for one hour. RPMI was added to the infected PBMCs and unabsorbed virus in the supernatant fluid was removed following centrifugation. The cells were resuspended in 10 mL RPMI (20% FCS, 30 units IL-2/mL) and placed in a 25 $cm^2$ tissue culture flask. The virus control flask contained infected cells only. Similar flasks contained efavirenz or the cytotoxic drug added separately or in combination. Flasks were incubated at 37° C., in 5% $CO_2$ for 3 days. On day 4, the contents of each flask were centrifuged and the supernatant, inactivated with 0.5% Triton X-100, was frozen at −70° C. for p24 analysis. The infected PBMCs were resuspended in RPMI, centrifuged again, and the supernatant discarded to remove residual drugs. The pellets were resuspended in each flask, and $1\times10^{e6}$ MT-2 cells were added. The final volume was 10 mL RPMI (5% FCS) per flask. After 4 more days of incubation (day 8), supernatant from each flask was inactivated with Triton X-100 and frozen at −70° C. The p24 antigen concentration of viral supernatants from days 4 and 8 was determined using the NEN Life Science Products HIV-1 p24 antigen capture assay.

The results presented indicate that in a combination therapy comprising a non-nucleoside reverse transcriptase HIV inhibitor and a carefully chosen cytotoxic agent will be effective in treating patients infected with HIV by selective eradication of the virus. The method of the present invention provides important advantages over currently available treatments for HIV infection.

DOSAGE AND FORMULATION

The NNRTI and cytotoxic compounds of this invention can be administered as treatment for viral infections by any means that produces contact of the active agent with the agent's site of action, i.e., the NNRTI, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, 17th ed., Mack Publishing Company, Easton, Pa., 1985, a standard reference text in this field, the disclosure of which is hereby incorporated by reference.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Combination of Components (i) and (ii)

Each therapeutic agent component of this invention can independently be in any dosage form, such as those described above, and can also be administered in various ways, as described above. In the following description component (ii) is to be understood to represent one or more agents as described previously. Thus, if components (i) and (ii) are to be treated the same or independently, each agent of component (ii) may also be treated the same or independently.

Components (i) and (ii) of the present invention may be formulated together, in a single dosage unit (that is, combined together in one capsule, tablet, powder, or liquid, etc.) as a combination product. When component (i) and (ii) are not formulated together in a single dosage unit, the component (i) may be administered at the same time as component (ii) or in any order; for example component (i) of this invention may be administered first, followed by administration of component (ii), or they may be administered in the reverse order. If component (ii) contains more that one agent, e.g., one RT inhibitor and one NNRTI, these agents may be administered together or in any order. When not administered at the same time, preferably the administration of component (i) and (ii) occurs less than about one hour apart. Preferably, the route of administration of component (i) and (ii) is oral. The terms oral agent, oral inhibitor, oral compound, or the like, as used herein, denote compounds which may be orally administered. Although it is preferable that component (i) and component (ii) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (i) and (ii) of the present invention will be readily ascertainable by a medical practitioner skilled in the art, based upon the present disclosure. By way of general guidance, typically a daily dosage may be about 100 milligrams to about 1.5 grams of each component. If component (ii) represents more than one compound, then typically a daily dosage may be about 100 milligrams to about 1.5 grams of each agent of component (ii). By way of general guidance, when the compounds of component (i) and component (ii) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose or other appropriate materials as known in the art, in order to further separate the active components. The polymer coating serves to form an additional barrier to interaction with the other component. In each formulation wherein contact is prevented between components (i) and (ii) via a coating or some other material, contact may also be prevented between the individual agents of component (ii).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Obviously, numerous modifications and variations of the present invention are possible in light of the above teachings. It is therefore to be understood that within the scope of the appended claims, the invention may be practiced otherwise than as specifically described herein.

What is claimed is:

1. A method of treating human immunodeficiency virus (HIV) infection in a mammal consisting essentially of administering in combination to a mammal in need thereof, a therapeutically effective amount of: (i) a cytotoxic agent selected from the group consisting of losoxantrone and etoposide; and (ii) a non-nucleoside reverse transcriptase HIV inhibitor, wherein said non-nucleoside reverse transcriptase inhibitor is efavirenz.

* * * * *